(12) United States Patent
Nakajima et al.

(10) Patent No.: US 7,153,295 B2
(45) Date of Patent: Dec. 26, 2006

(54) DISPOSABLE DIAPER

(75) Inventors: Kaiyo Nakajima, Kagawa-ken (JP); Yoshitaka Mishima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 163 days.

(21) Appl. No.: 10/714,941

(22) Filed: Nov. 18, 2003

(65) Prior Publication Data

US 2004/0143233 A1    Jul. 22, 2004

(30) Foreign Application Priority Data

Nov. 20, 2002    (JP) .............................. 2002-336842

(51) Int. Cl.
A61F 13/15    (2006.01)

(52) U.S. Cl. .............................. 604/385.101; 604/380; 604/383; 604/385.24; 604/385.01; 604/385.28

(58) Field of Classification Search ........... 604/385.17, 604/385.18, 385.101, 385.01, 385.04, 385.05, 604/385.24–385.3, 385.09, 379, 380, 383
See application file for complete search history.

(56) References Cited

U.S. PATENT DOCUMENTS

| | | | |
|---|---|---|---|
| 4,589,876 A * | 5/1986 | Van Tilburg ............ | 604/385.04 |
| 4,950,262 A * | 8/1990 | Takagi .................. | 604/385.101 |
| 5,062,840 A | 11/1991 | Holt et al. | |
| 5,290,262 A * | 3/1994 | Vukos et al. .......... | 604/385.17 |
| 5,607,416 A * | 3/1997 | Yamamoto et al. ......... | 604/397 |
| 6,056,732 A * | 5/2000 | Fujioka et al. .......... | 604/385.01 |
| 6,120,485 A * | 9/2000 | Gustafsson et al. .... | 604/385.19 |
| 6,123,692 A * | 9/2000 | Guidotti et al. ........ | 604/385.01 |
| 6,132,409 A * | 10/2000 | Vogt et al. ................... | 604/348 |
| 6,264,641 B1 * | 7/2001 | Van Gompel et al. .. | 604/385.22 |
| 6,423,042 B1 * | 7/2002 | Sasaki ................... | 604/385.01 |
| 6,464,673 B1 | 10/2002 | Ben Natan | |
| 2002/0111594 A1 | 8/2002 | Onishi et al. | |

FOREIGN PATENT DOCUMENTS

| | | |
|---|---|---|
| BE | 1 010 807 | 2/1999 |
| EP | 0 908 162 | 4/1999 |
| EP | 1 059 073 | 12/2000 |
| EP | 1 297 809 | 4/2003 |
| JP | 6-5614 | 1/1994 |
| JP | 6-24624 | 3/1994 |
| WO | 93 12748 | 7/1993 |
| WO | 98 17219 | 4/1998 |

OTHER PUBLICATIONS

Patent Abstracts of Japan, Publication No. 08196565, Aug. 6, 1996.

* cited by examiner

*Primary Examiner*—Jacqueline F. Stephens
(74) *Attorney, Agent, or Firm*—Lowe Hauptman & Berner LLP

(57) ABSTRACT

A disposable diaper includes a top sheet, a back sheet, and a liquid absorbent core disposed therebetween. The diaper has openings, which pass through the top sheet and the core, and are formed in at least the crotch region of the diaper. The back sheet has a free portion which is disposed beneath the core and extendible downwards in its thickness direction. The back sheet further has a fixed edge portion which is outside an outer periphery of the free portion and fixed to the top sheet. A plurality of longitudinally extending contractible elastic members are disposed at least in the free portion and the fixed edge portion. A plurality of transversely extending gathers are formed under the contraction of the elastic members.

20 Claims, 8 Drawing Sheets

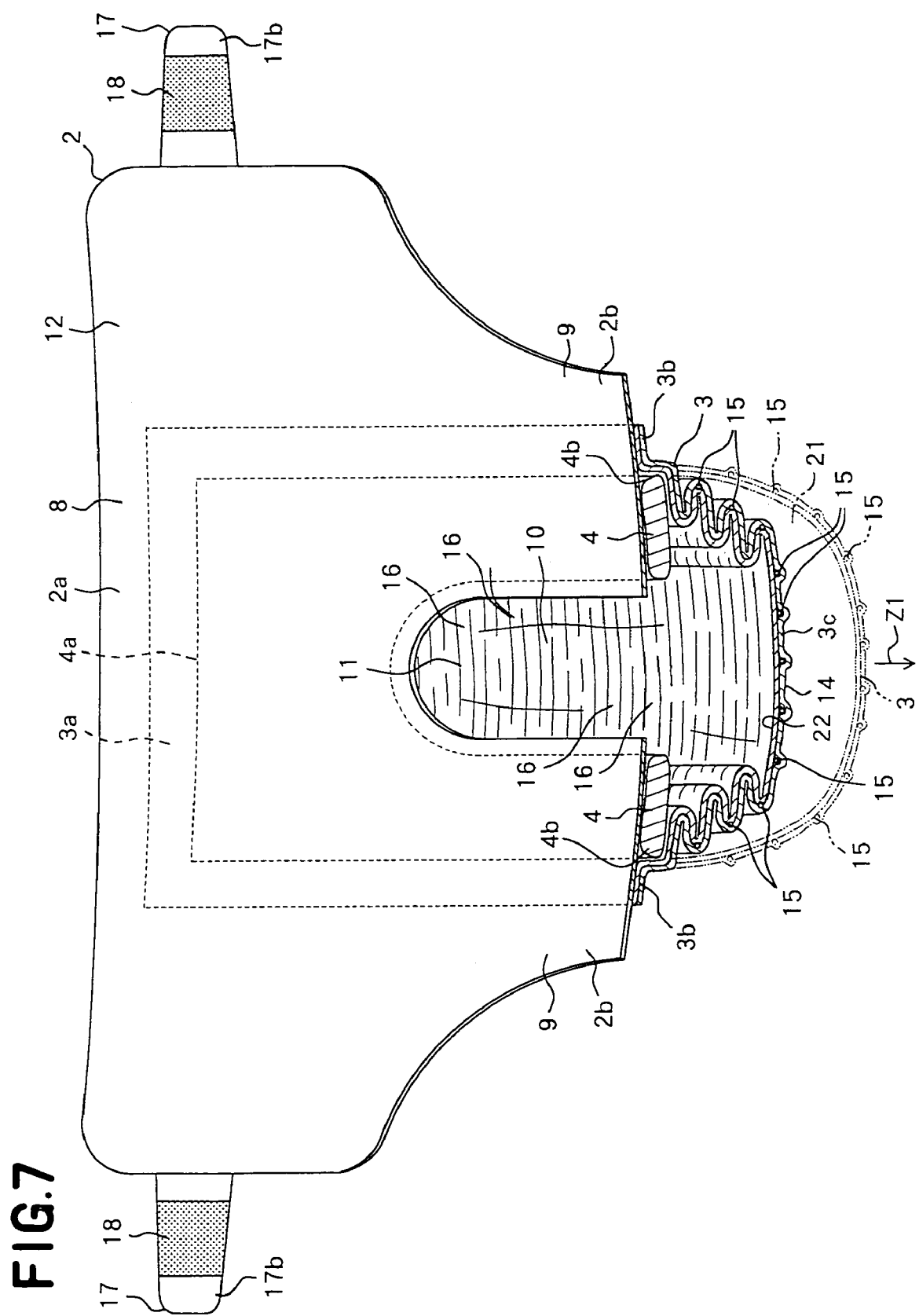

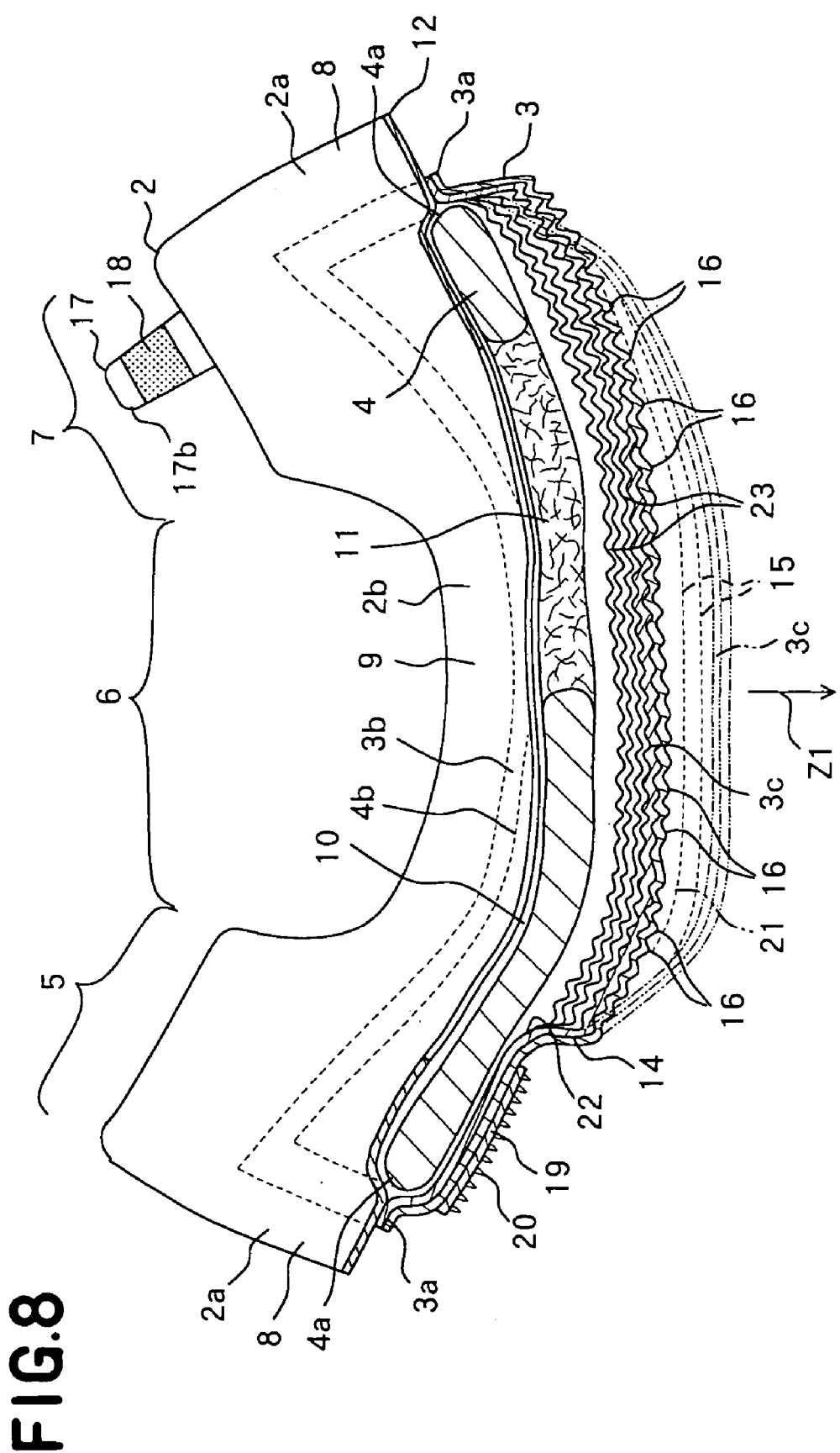

DISPOSABLE DIAPER

BACKGROUND OF THE INVENTION

The present invention relates to a disposable diaper which absorbs and contains body exudates. The present application is based on, and claims priority from, Japanese Application Serial Number 2002-336842, filed Nov. 20, 2002, the disclosure of which is hereby incorporated in its entirety.

The Japanese Utility Model documents 1 and 2 listed below disclose disposable diapers each comprising a liquid pervious top sheet disposed on the body contactable side, a liquid impervious back sheet disposed away from the body of the wearer and an absorbent core disposed between the top sheet and the back sheet, and being provided with a front waist region and a back waist region in a longitudinal direction and a crotch region which is positioned between these waist regions, wherein the absorbent core has a depressed portion where the core caves in from the top surface towards the under surface in its thickness direction.

The diaper disclosed in the Japanese Utility Model document 1 comprises an absorbent core which has a circular depressed portion caving in from the top surface towards the under surface in its thickness direction. Openings whose one end each opens into the open surface of the depressed portion are formed in the top sheet of the diaper. The depressed portion is formed in a transversely middle zone of the crotch region, and the top sheet positioned above the open surface of the depressed portion forms a valve section extending from the opening edge towards the opening center of the depressed portion. The body exudates discharged while it is worn go through the openings in the top sheet to be contained in the depressed portion of the core.

In the diaper disclosed in the Japanese Utility Model document 2, the core has a circular depressed portion where the core caves in from the top surface towards the under surface in its thickness direction and the top sheet which is infolded into the depressed portion is secured to the peripheral and bottom surfaces of the depressed portion. The body exudates discharged while it is worn are contained in the depressed portion of the core.

Japanese Utility Model Document 1

Japanese Utility Model Application Publication No. 6-5614A

Japanese Utility Model Document 2

Japanese Utility Model Application Publication No. 6-21624A

SUMMARY OF THE INVENTION

In the diapers disclosed in the Japanese Utility Model documents 1 and 2, the liquid content out of the body exudates contained in the depressed portion of the core is absorbed in the core, while the solid content remains in the depressed portion. Since the diapers are not capable of keeping the solid content away from the crotch of the wearer, the depressed portion will be compressed when the body weight of the wearer is applied to the diaper, resulting possibly in the solid content being pushed back to the outer surface of the top sheet and soiling the crotch of the wearer.

Also, the diapers are not able to contain a large amount of excrement in the depressed portion due to their limited capacity, and when a large amount of excrement is discharged while worn, such portion of the excrement as the depressed portion can not afford to contain may be diffused over the outer surface of the top sheet and soil a large area of the crotch of the wearer.

It is an object of the present invention to provide a disposable diaper which is capable of keeping the excrement discharged away from the crotch of the wearer and preventing it from soiling the crotch of the wearer.

According to the present invention, there is provided a disposable diaper comprising a top sheet facing the wearer, a liquid impervious back sheet facing away from the wearer, and a liquid absorbent core disposed between the top and back sheets; a front waist region; a back waist region; a crotch region which is positioned between the front and back waist regions; end flaps which are outside respective end edges of the core and extend in a transverse direction of the diaper therefrom; side flaps which are outside respective side edges of the core and extend in a longitudinal direction of the diaper therefrom; and openings which pass through a thickness of the top sheet and the core and are formed in at least the crotch region out of the front and back waist regions and the crotch region.

The present invention further comprises a back sheet having a free portion which is underbeneath the core and extendible downwards in a thickness direction of the diaper and a fixed edge portion which defines an outer periphery of the free portion and fixed to the top sheet, a plurality of elastic members extending in the longitudinal direction of the diaper and disposed at a given interval in a transverse direction of the diaper being contractibly attached to at least the free portion out of the free portion and the fixed edge portion; and a plurality of gathers extending in the transverse direction and formed under contraction of said elastic members.

The present invention includes the following embodiments:

The top sheet is stretchable/contractible.

The back sheet is small in area than the top sheet, and a greater part of the side flaps is formed out of side portions of the top sheet which extend outwards from respective side edges of the core in the transverse direction.

A greater part of the end flaps is formed out of end portions of the top sheet which extend outwards from respective end edges of the core in the longitudinal direction.

A longitudinal dimension of the back sheet, when the gathers are extended in the longitudinal direction against the contracting force of the elastic members, ranges 1.05 to 4.0 times a longitudinal dimension of the back sheet in a state in which the gathers are formed.

A tensile stress of the elastic member ranges 0.098 to 1.96 N when stretched to 100% of its initial length.

A plurality of pleats extending in the longitudinal direction of the diaper are further formed in the back sheet by folding the back sheets in the transverse direction with the pleats being arranged at a given interval in the transverse direction.

A transverse dimension of the back sheet, when the pleats are extended in the transverse direction, ranges 1.5 to 3.0 times that of the back sheet in a state where the pleats are formed.

The back sheet comprises one of a composite sheet made of a hydrophobic nonwoven fabric and a breathable but liquid impervious plastic film overlaid and joined together and a composite nonwoven fabric made of a plurality of hydrophobic nonwoven fabrics overlaid and joined together.

BRIEF DESCRIPTION OF THE DRAWING

FIG. 7 is a sectional view taken along section line VII—VII in FIG. 5.; and

FIG. 8 is a sectional view taken along section line VIII—VIII in FIG. 5.

DETAILED DESCRIPTION OF THE PREFERRED EMBODIMENTS

Figure 1:
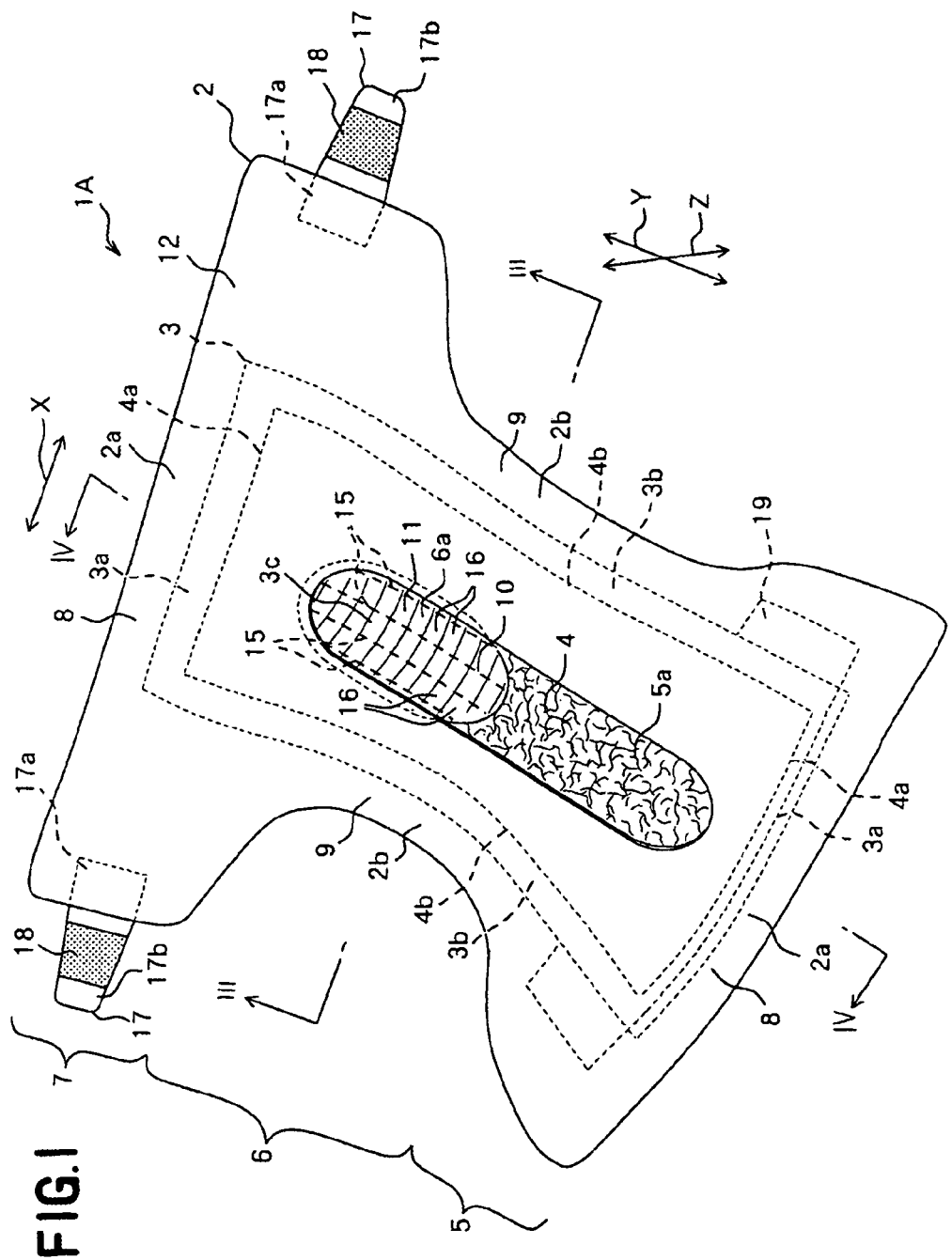
FIG. 1 is a partially cutaway perspective view of a diaper shown as one example.
Figure 2:
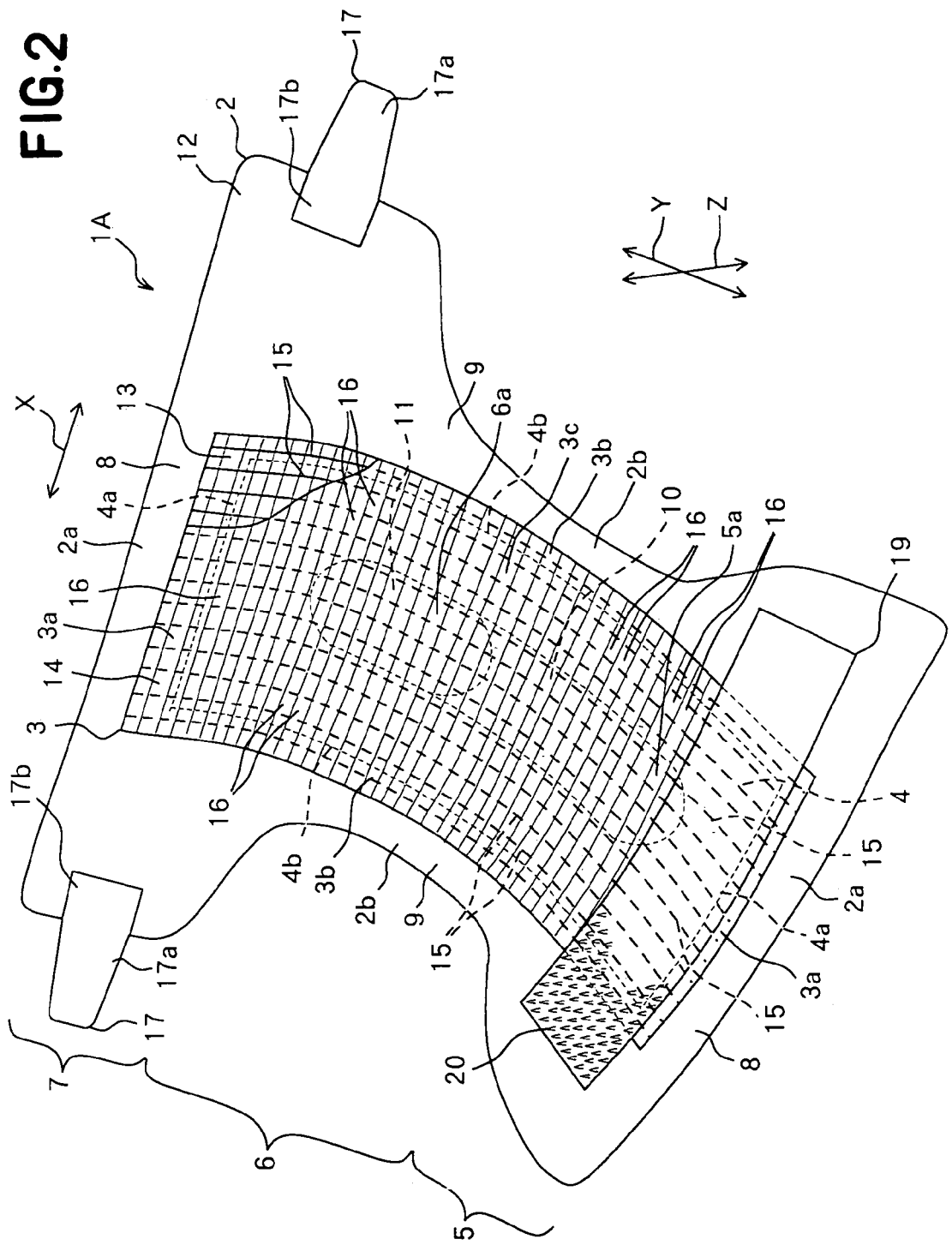
FIG. 2 is a perspective view showing the diaper from the side of the back sheet in FIG. 1.
Figure 3:
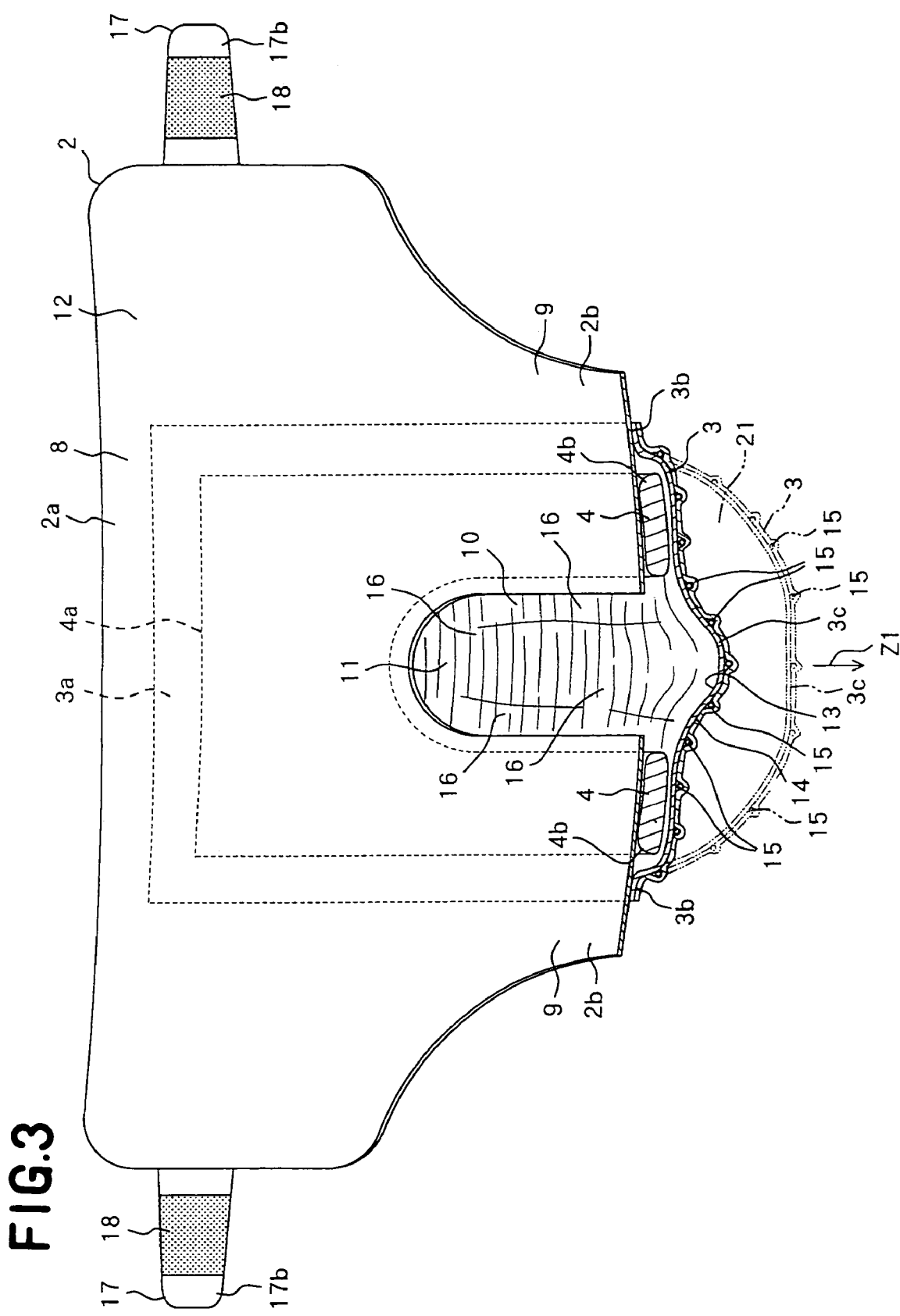
FIG. 3 is a sectional view taken along section line III—III in FIG. 1.
Figure 4:
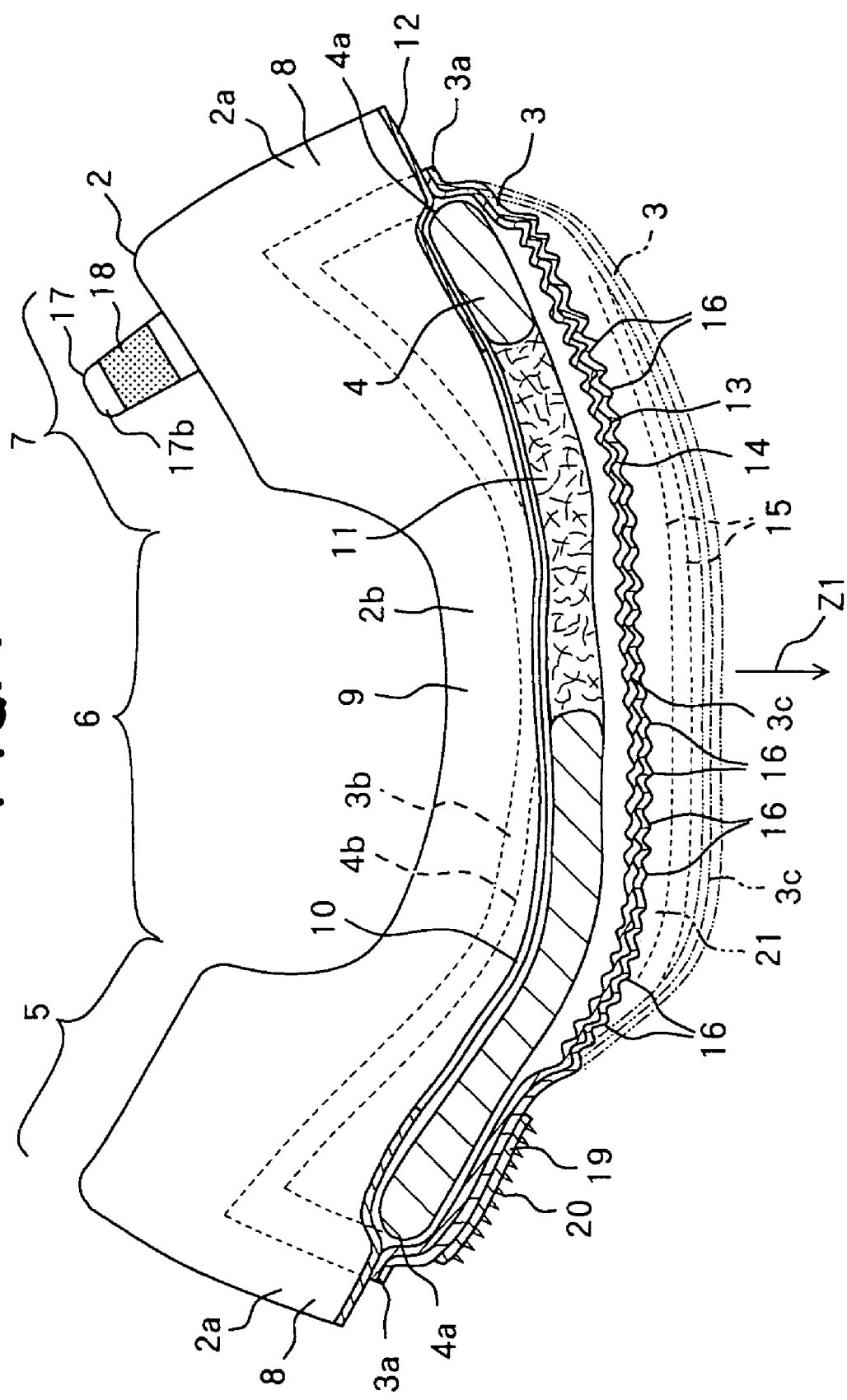
FIG. 4 is a sectional view taken along section line IV—IV in FIG. 1.

Details of a disposable diaper according to the present invention will be more fully understood from the description given hereunder with reference to the accompanying drawings FIG. 1 is a partially cutaway perspective view of a diaper 1A shown as one embodiment. FIG. 2 is a perspective view showing the diaper 1A in FIG. 1 from the side of the back sheet 3. FIG. 4 is a sectional view taken along section line III—III in FIG. 1. FIG. 4 is a sectional view taken along section line IV—IV in FIG. 1. In FIGS. 1 and 2, the transverse, longitudinal and thickness directions are indicated with arrows X, Y and Z, respectively. In FIGS. 3 and 4, a state in which the free portion 3c of the back sheet 3 of the diaper 1A is extended downwards in a thickness direction is shown with chain double-dashed lines. The inner surfaces of the top sheet 2 and the back sheet 3 mean the surfaces opposite to the core 4, respectively, and the outer surface of the sheets 2 and 3 mean the surfaces unopposite to the core 4, respectively.

The diaper 1A comprises a top sheet 2 that contacts the body of the wearer, a back sheet 3 that faces away from the body of the wearer, and a liquid absorbent core 4 that is disposed between the top and back sheets. The diaper 1A has a front waist region 5 and a back waist region 7 in a longitudinal direction and a crotch region 6 positioned between the waist regions 5 and 7. The diaper 1A is of an open type in which the front and back waist regions 5 and 7 are connected when it is to be worn. The core 4 extends between the front and back waist regions 5 and 7, being joined to the inner surface of the top sheet 2. The whole area of the top surface and the under surface of the core 4 is covered with the top sheet 2 and the back sheet, respectively.

The diaper 1A has a pair of end flaps 8 positioned outside the end edges 4a of the core 4, each extending in the transverse direction therefrom and a pair of end flaps 9 positioned outside the side edges 4b, each extending in the longitudinal direction therefrom. The side flaps 9 form an arch inwardly, respectively, in a transverse direction of the diaper 1A. The diaper 1A presents generally an hourglass shape in its plane figure.

In the top sheet 2, an upper opening 10 which are elongate and round in its ends is formed so as to pass from the inner surface through to the outer surface. Similarly, in the core 4, a lower opening 11 which are elongate and round in its ends is formed so as to pass from the inner surface through to its external surface. The upper opening 10, which is larger in area than the lower opening 11 are formed approximately in the whole area of the crotch region and in the back half of the front waist region 5 in the transversely middle zones 5a and 6a of the front waist region 5 and the crotch region 6. The lower opening 11 is communicated to the upper opening positioned in the back half of the back waist region 7.

The top sheet 2 has end portions 2a extending outwards in a longitudinal direction from the respective end edges 4a of the core 4 and side portions 2b extending outwards in a transverse direction from the respective side edges 4b of the core 4. The top sheet 2 comprises a nonwoven fabric 12 which is elastically contractible in both longitudinal and transverse directions. The nonwoven fabric 12 can be either hydrophilic or hydrophobic.

The back sheet 3, which is smaller in area than the top sheet 2, has fixed end portions 3a each extending outwards in a longitudinal direction from the respective end edge 4a of the core 4 fixed side edge portions 3b each extending outwards in a transverse direction from the respective side edges 4b of the core 4, and a free portion 3c extending between the end portions 3a and the side portions 3b. The free portion 3c is disposed beneath the core 4 and is partially exposed from the upper and lower openings 10, 11. The free portion 3c is not joined to either the top sheet 2 or the core 4, being separatable therefrom. The back sheet 3 comprises a composite sheet made of a breathable but liquid impervious plastic film 13 and a hydrophobic fibrous nonwoven fabric 14 overlaid and joined together. The nonwoven fabric 14 is disposed outside the film 13.

A plurality of stretchable and contractible elastic members 15 extending in the longitudinal direction, which are disposed at given intervals in a transverse direction, are contractibly secured to in the free portion 3c as well as the end portions 3a, side portions 3b of the back sheet 3, being disposed and joined between the film 13 and the nonwoven fabric 14.

The back sheet 3 has a plurality gathers 16 undulating up and down in a thickness direction of the diaper 1A, which gathers 16 are formed under the contraction of the elastic members 15 in a longitudinal direction. The gathers 16 extend discontinuously in a transverse direction, while they are arranged almost continuously in the longitudinal direction. As illustrated in FIG. 4, the free portion 30 formed with the gathers 16 is capable of convexly curve downwards in a thickness direction of the diaper 1A. The free portion 3c of the back sheet 3 is extendible downwards in a thickness direction of the diaper 1A as the gathers 16 are smooth out.

The core 4 comprises a mixture of fluff pulp and superabsorbent polymer particles or a mixture of fluff pulp, superabsorbent polymer particles and thermoplastic synthetic resin fibers, being compressed into a given thickness. The core 4 is preferably wrapped in its entirety with a liquid pervious sheet such as tissue paper and hydrophilic nonwoven fabric so as to prevent its deformation or to prevent the polymer particles from dropping out. Starchy, cellulosic and synthetic polymer materials can be used for such polymer particles. When the body exudates permeate into the core 4, it swells by a given rate as the polymer particles absorb the liquid content of such body exudates.

In the end flaps 8, the end portions 3a of the back sheet 3 extend slightly outwards beyond the respective end edges 4a of the core 4 in a longitudinal direction and the end edges 2a of the top sheet 2 extend further outwards beyond the respective end portions 3a of the back sheet 3 in a longitudinal direction. A greater part of the end flaps 8 comprise the end portions 2a of the top sheet 2. The end portions 2a and 3a of the top and back sheets 2 and 3, respectively, are overlapped with each other and the inner surfaces of the top and back sheets 2 and 3 are joined to each other at the end portions 2a and 3a, respectively.

In the side flaps 9, the side portions 3b of the back sheet 3 extend slightly outwards beyond the side edges 4b of the core 4 in a transverse direction, and the side portions 2b of the top sheet 2 extend outwards further beyond the respective side portions 3b of the back sheet 3 in a transverse direction. A greater part of the side flaps 9 comprise the side portions 2b of the top sheet 2. The side portions 2b and 3b of the top and back sheets 2 and 3, respectively, are overlaid with each other and the inner surfaces of the top and back sheets 2 and 3 are joined to each other at the side portions 2b and 3b, respectively.

The side flaps 9 of the back waist region 7 are attached with flexible tape fasteners 17 made of a plastic film. The tape fastener 17 has a fixed end section 17a secured to the inner surface of the top sheet 2 and a free end section 17b extending outwards beyond the fixed end section 17a in a transverse direction. The free end section 17b is attached with a hook member 18 of a mechanical fastener. The front waist region 5 is attached with a flexible target tape 19 which releasably attaches the tape fastener 17. The target tape 19 is formed from a loop member 20 of the mechanical fastener, and has a rectangular shape longer in the transverse direction being secured to the inner surface of the top sheet 2 and to the outer surface of the back sheet 3.

In order to wear the diaper 1A, the side flaps 9 in the back waist region 7 are overlapped with the side flaps 9 in the front waist region, the free end section 17a of the tape fastener 17 is attached to the target tape 19 by engaging the hook member 18 with the loop member 20, and the front waist region 5 and the back waist region 7 are connected. In the diaper 1A whose front and back waist regions 5 and 7 are connected, a waist opening and a pair of leg openings are formed (not shown), as in a parts or pull-on type.

Excrement discharged while the diaper 1A is worn is received by the inner surface of the free portion 3c of the back sheet 3 through the upper and lower openings 10 and 11. In the back sheet 3, as the gathers 16 which are formed in the free portion 3c extend in the longitudinal direction by weight of the excrement, generally smoothing out of resulting in disappearing, the free portion 3c extends downwards in a thickness direction of the diaper 1A, namely curves in the direction shown by the arrow Z1, as illustrated by chain double-dashed lines in FIGS. 3 and 4. When the gathers 16 are smoothed out, a fecal material receiving space 21 capable of containing the excrement is formed between the free portion 3c of the back sheet 3 and the core 4. The liquid content in the excrement is absorbed into the core 4, while the solid content is held in the space 21. Urine discharged while the diaper 1A is worn permeates and passes through the upper open 10 to be absorbed by the core 4. The diaper 1A ensures that the excrement can be prevented from soiling the crotch region of the wearer since a large amount of excrement, if discharged while it is worn, can be contained and held in the space 21, and thus the excrement will not stay on, nor get diffused over, the outer surface of the top sheet 2.

Since the top sheet 2 and the core 4 are disposed between the excrement contained in the space 21 and the crotch region of the wearer in the diaper 1A, the excrement can be kept away from the crotch region of the wearer. In the diaper 1A, since the top sheet 2 and the core 4 serve as barrier to the excrement contained in the space 21, the excrement will not pushed out of the space 21 back to the outer surface of the top sheet 2 if body weight of the wearer is applied to compress the diaper 1A. In the diaper 1A prior to discharge of excrement, since the gathers 16 of the back sheet 3 are maintained by means of contracting force of the elastic members 15, the free portion 3c of the back sheet 3 will not be extended and curved downwards in a thickness direction of the diaper 1A.

If the core 4 expands in volume as the polymer particles absorb water, the free portion 3c of the back sheet 3 contains the increased volume of the core 4 as the free portion 3c extends downwards in a thickness direction of the diaper 1A.

Since a greater part of both the end flaps 8 and the side flaps 9 is made of the stretchable/contractible top sheet 2, the diaper 1A, when worn, can be fastened around the waist part of the wearer by means of contracting force of the end flaps 8 and that of the side flaps 9 in the back waist region 7, and thus, the diaper 1A can be prevented from sliding down from where it is applied to the wearer. Also, the diaper 1A, when worn, can be fastened around the legs of the wearer by means of contracting force of the side flaps 9 to prevent body exudates from leaking from the gaps between the diaper and the legs of the wearer in both sides of the crotch region 6.

When the gathers 16 are elongated in the longitudinal direction against a contracting force of the elastic members 15, the longitudinal dimension of the back sheet 3 ranges 1.05 to 4.0 times, more preferably 2.5 to 3.0 times, the length of the back sheet 3 in a state where the gathers 16 are formed. In case the above ratio of elongation in the longitudinal direction is below 1.05, the space 21 which is formed between the free portion 3c of the back sheet 3 and the core 4 will not be large enough to contain a large amount of excrement therein. In case the above ratio of elongation in the longitudinal direction exceeds 4.0 times, the free portion 3c will result in too extending downwards in a thickness direction of the diaper 1A.

The elastic member 15 has a tensile stress ranges 0.098 to 1.96 N when tensile at 100%. In case the tensile stress of the elastic member 15 is below 0.098 N, a contracting force of the elastic member 15 may not be large enough to contract the back sheet 3 in the longitudinal direction and to form the gathers 16 in the back sheet 3 though it depends on rigidity of the back sheet 3. In case the tensile stress of the elastic member 15 exceeds 1.96 N, the contracting force of the elastic member 15 can be too great for the gathers 16 to be elongated with the weight of excrement and resultingly to have a space 21 formed between the free portion 3c of the back sheet 3 and the core 4. The tensile stress of the elastic member 15 was measured according to the following method:

(1) Elastic members (150 mm long) for measurement equivalent to the elastic member 15 attached to the back sheet 3 as well as two slender rods are prepared. An end portion of an elastic member for measurement is wound around one end of a rod and similarly the other end portion around one end of the other rod, and the rod ends and the end portions of such elastic member are affixed with an adhesive tape.

(2) One rod is clamped with the chuck at one end of the tensile testing machine, and the other rod with the chuck at the other end, so that the elastic member for measurement is laid extended without sagging between a pair of the chucks.

(3) Autograph of Shimadzu Corporation in Japan is used as the tensile testing machine for the above measurement. Measurement of a tensile stress is conditioned by the chuck-to-chuck distance at 100 mm (the chuck-to-chuck distance for the measuring elastic member at 100 mm)

and the speed of testing at 100 mm/min., and the tensile stress of the measuring elastic member when elongated up to 200 mm (100%) is measured with the Autograph. The tensile stress was measured with a plurality of the measuring elastic members and their average value is employed as the tensile stress of the elastic member 15.

Figure 5:
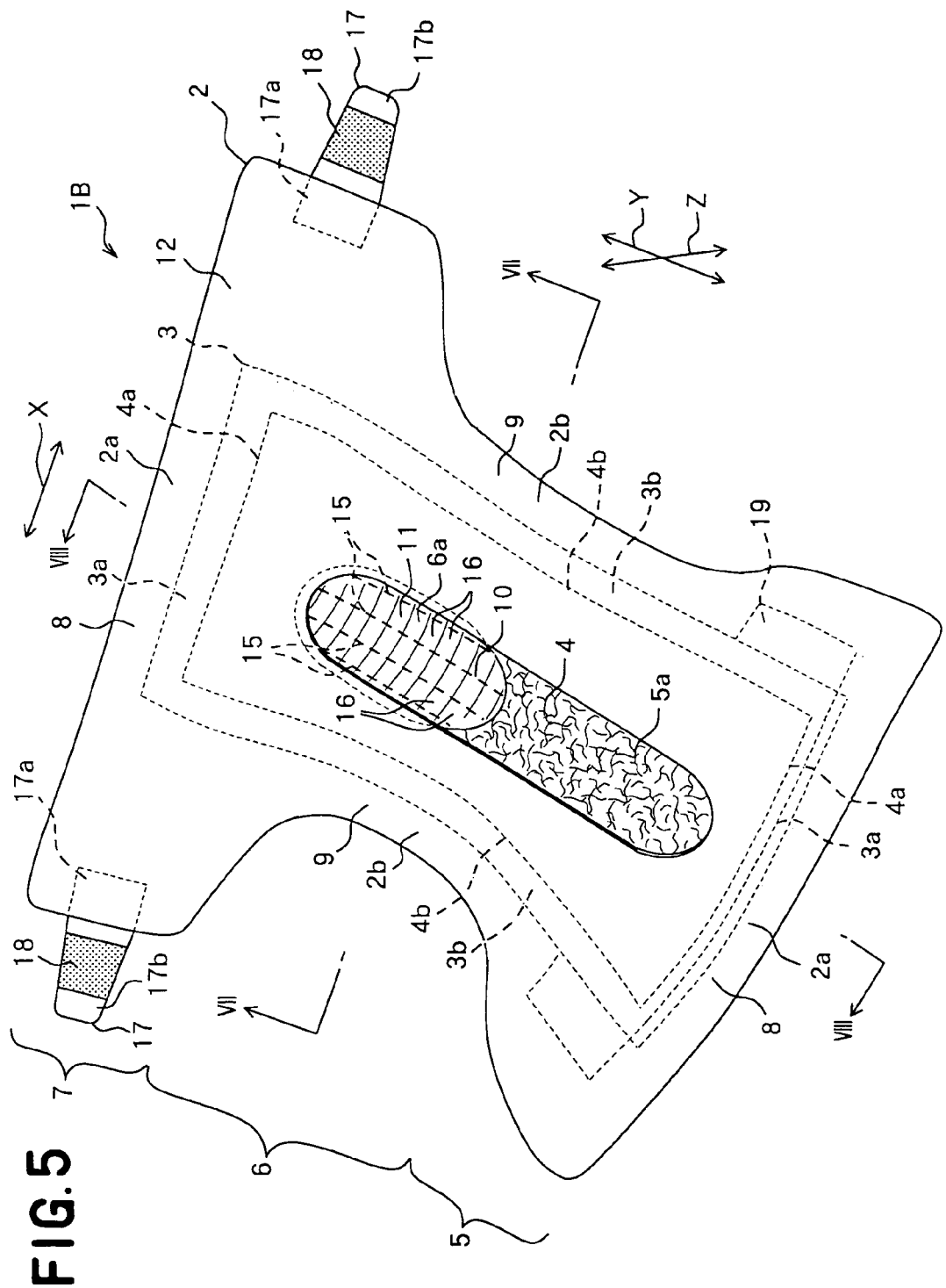
FIG. 5 is a partially cutaway perspective view of a diaper shown as an alternative example.
Figure 6:
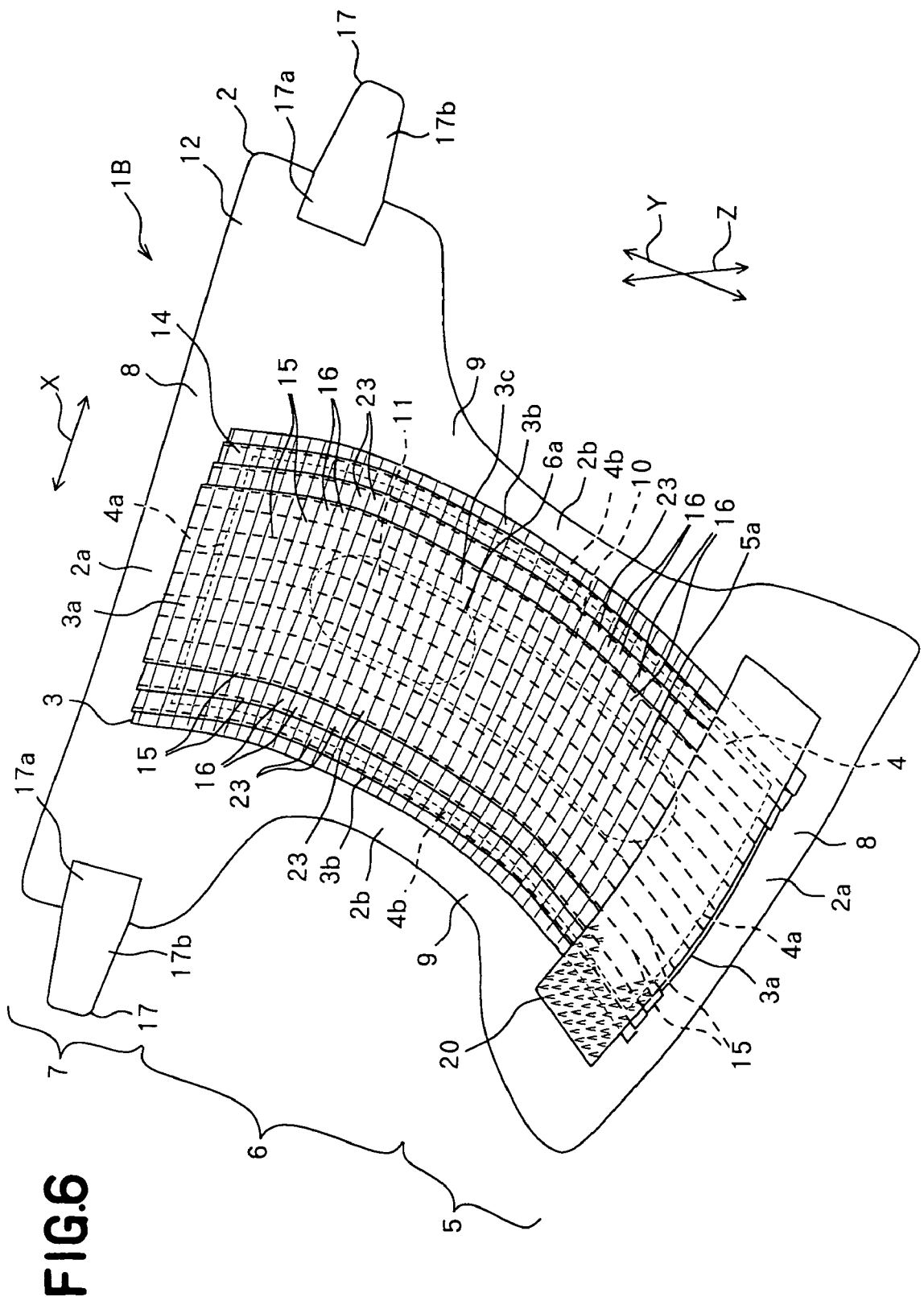
FIG. 6 is a perspective view showing the diaper from the side of the back sheet in FIG. 5.

FIG. 5 is a partially cutaway perspective view of a diaper 1B shown as another embodiment. FIG. 6 is a perspective view showing the diaper 1B from the side of the back sheet in FIG. 5. FIG. 7 is a sectional view taken along section line VII—VII in FIG. 5. FIG. 8 is sectional view taken along section line VIII—VIII in FIG. 5. In FIGS. 5 and 6, the transverse, longitudinal and thickness directions are shown by arrow marks X, Y and Z, respectively. In FIGS. 7 and 8, a state in which the free portion 3c of the back sheet 3 is elongated downwards in a thickness direction of the diaper 1B is shown with chain double-slashed lines.

The diaper 1B comprises a top sheet 2, a back sheet 3, and an absorbent core which is disposed between the top and back sheets 2 and 3. The diaper 1B has a front waist region 5, a back front region 7, and a crotch region 6 positioned between the waist regions 5 and 7. The diaper 1B has a pair of end flaps 8 extending in a transverse direction and a pair of side flaps extending in a longitudinal direction. The core 4 extending between the front and back waist regions is joined to the inner surface of the top sheet 2. The core 4 is identical to the one illustrated in FIG. 1.

The upper opening 10 which is elongate and round in its ends is formed in the top sheet 2, passing through the thickness between the inner and outer surfaces. Similarly, the lower opening 11 which is elongate and round in its ends is formed in the core 4, passing through its thickness between the inner and outer surfaces. The upper opening 10 is formed approximately in the whole area of the crotch region 6 and in the back half of the front waist region 5, being disposed in the transversely middle zones 5a and 6a of the front waist region 5 and the crotch region 6. The lower opening 11 is positioned in the back half of the back waist region 7.

The top sheet 2 has end portions 2a extending in the transverse direction and side portions 2b extending in the longitudinal direction. The top sheet 2 comprises a nonwoven fabric 12 having elastic expandability and contractibility in both transverse and longitudinal directions. The back sheet 3, which is smaller in area than the top sheet 2 has fixed side portions 3a extending in the transverse direction, fixed side portions 3b extending in the longitudinal direction, and a free portion 3c extending between the end portions 3a and the side portions 3b. The free portion 3c of the back sheet 3 is disposed beneath the core 4 and it is partially exposed from the upper and lower openings 10, 11. The free portion 3c is not joined to either the top sheet 2 or the core 4, being separatable therefrom.

The back sheet 3 comprises a composite nonwoven fabric made of two sheets of hydrophilic nonwoven fabrics 14 and 22 overlaid with each other. A plurality of pleats 23 which extend in a longitudinal direction while time being arranged at a given interval in a transverse direction are formed in the back sheet 3. The pleats 23 are formed by folding the free portion 3c in the form of zigzag at cross section in a transverse direction, so that the free portion 3c is formed so as to be convexly curved downwards in a thickness direction of the diaper 1B (see FIG. 7).

A plurality of stretchable/contractible elastic members 15 extending in the longitudinal direction as arranged at a given interval in a transverse direction are contractively attached to the free portions 3. The elastic members 15 which are disposed between the nonwoven fabrics 14 and 22 are secured between the nonwovens 14 and 22. A part of the elastic members are disposed in the folded portion of the pleats 23. A plurality of gathers 16 undulating in a thickness direction of the diaper 1B are formed in the back sheet 3 under the contraction of the elastic members 15 in a longitudinal direction. The gathers 16 extend discontinuously in a transverse direction, while they are disposed almost continuously in a longitudinal direction. The free portion 3c formed with the gathers 16 is extendible downwards in a thickness direction of the diaper 1B as the gathers 16 are smoothed out in a longitudinal direction while the pleats 23 are unfolded in a transverse direction.

In the end flaps 8, the end portions 3a of the back sheet 3 extend slightly outwards beyond the end edges 4a of the core 4 in a longitudinal direction and the end edges 2a of the top sheet 2 extend further outward beyond the end portions 3a of the back sheet 3 in a longitudinal direction. A greater part of the end flaps 8 comprise the end portions 2a of the top sheet 2. The end portions 2a and 3a of the top and back sheets 2 and 3, respectively, overlap with each other and the inner surfaces of the sheets 2 and 3 are joined to each other at the end portions 2a and 3a.

In the side flaps 9, the side portions 3b of the back sheet 3 extend slightly outwards beyond the side edges 4b of the core 4 in a transverse direction, and the side portions 2b of the top sheet 2 extend outwards further beyond the side portions 3b of the back sheet 3 in a transverse direction. A greater part of the side flaps 9 comprise the side portions 2b of the top sheet 2. The side portions 2b and 3b of the top and back sheets 2 and 3, respectively, overlap with each other and the inner surfaces of the sheets 2 and 3 are joined to each other at the side portions 2b and 3b.

The side flaps 9 of the back waist region 7 are attached with tape fasteners 17 having hook members 18 at the free end portions 17b. The front waist region 5 is attached with a target tape 19 of a transversely oblong rectangle which releasably attaches the tape fastener 17. The target tape 19 is formed from a loop member 20. The sequence of putting on this diaper 1B is identical to the one illustrated in FIG. 1.

Excrement discharged while the diaper 1B is worn is received by the inner surface of the free portion 3c of the back sheet 3 through the upper and lower 10 and 11. In the back sheet 3, as the gathers 16 which are formed in the free portion 3c extend in the longitudinal direction and at the same time the pleats 23 which are formed in the free portion 3c extend in the transverse direction by weight of the excrement, the free portion 3c further convexly curves downwards in a thickness direction of the diaper 1B as indicated by the arrow Z1, as illustrated by chain double-dashed lines in FIGS. 7 and 8. As the pleats 23 are unfolded with smooth out by the extension of the gathers 16, the fecal material receiving space 21 capable of containing the excrement is formed between the free portion 3c of the back sheet 3 and the core 4. The liquid content in the excrement is absorbed with the core 4, while the solid content is held in the space 21.

The diaper 1B ensures that the excrement can be prevented from soiling the crotch region of the wearer since a large amount of excrement, if discharged while it is worn, can be contained and held in the space 21, and thus the excrement will not stay on, nor get diffused over, the outer surface of the top sheet 2. Since the top sheet 2 and the core 4 are disposed between the excrement contained in the space 21 and the crotch region of the wearer in the diaper 1B, the excrement can be kept away from the crotch region of the wearer. Since the top sheet 2 and the core 4 serve as a barrier to the excrement contained in the space 21, the excrement will not get out of the space 21 back to the outer, surface of the top sheet 2. In the diaper 1B prior to discharge of excrement, since the gathers 16 of the back sheet 3 are maintained by means of contracting force of the elastic members 15, the free portion 3c of the back sheet 3 will not be extended and curved downwards in a thickness of the diaper 1B.

If the core 4 swells as the polymer particles absorb water, the free portion 3c of the back sheet 3 contains the increased volume of the core 4 as the free portion 3c extends downwards in a thickness direction of the diaper 1B.

The diaper 1B allows the free portion 3c of the back sheet 3 to extend downwards in a thickness direction of the diaper 1B to a substantially larger degree leading to an enlarged volume of the space 21 than the diaper 1A illustrated in FIG. 1, due to formation of the gathers 16 and the pleats 23 in the back sheet 3 in the diaper 1B as compared with the diaper 1A in which the gathers 16 only are formed in the back sheet 3, as illustrated in FIG. 1.

In the diaper 1B, since a greater part of both the end flaps 8 and the side flaps 9 is made of the stretch top sheet 2, the diaper 1B, when worn, can be fastened around the waist part of the wearer by means of contracting force of the end flaps 8 and that of the side flaps 9 in the back waist region 7, and thus, the diaper 1B can be prevented from sliding down from where it is applied to the wearer. Also, the diaper 1B can be fastened around the legs of the wearer by means of contracting force of the side flaps 9 to prevent body exudates from leaking from the gaps between the diaper and the legs of the wearer in both sides of the crotch region 6.

When the gathers 16 are elongated in the longitudinal direction against contracting force of the elastic members 15, the longitudinal dimension of the back sheet 3 ranges 1.05 to 4.0 times, more preferably 2.5 to 3.0 times, the length of the back sheet 3 in a state where the gathers 16 are formed. When the pleats 23 are elongated in the transverse direction, the transverse dimension of the back sheet 3 ranges 1.5 to 3.0 times the transverse dimension of the back sheet 3 in a state where the pleats 23 are formed. In case the above ratio of elongation in a transverse direction is below 1.5, volume of the space 21, which is formed between the free portion 3c of the back sheet 3 and the core 4, can not be enlarged if the pleats 23 are extended in the transverse direction by weight of the excrement with no effect of forming the pleats 23 in the back sheet 3 to attain an increased volume of the space 21. In case the above ratio of elongation in the transverse direction exceeds 3.0 times, it is necessary to form more than necessary number of pleats in the back sheet 3 to avoid the back sheet 3 from slackening too extending downwards in a thickness direction of the diaper 1B.

In the diaper 1B, the elastic member 15 has a tensile stress which ranges 0.098 to 1.96 N when elongated at 100%. In case the tensile stress of the elastic member 15 is below 0.098 N, a contracting force of the elastic member 15 may not be large enough to contract the back sheet 3 in the longitudinal direction and to form the gathers 16 in the back sheet 3. In case the tensile stress of the elastic member 15 exceeds 1.96 N, the contracting force of the elastic members 15 can be too great for the gathers 16 to be elongated with the weight of excrement and resultingly to have a space 21 formed between the free portion 3c of the back sheet 3 and the core 4. The method for measurement of the tensile stress of the elastic member 15 is the same as depicted in FIG. 1.

The stretchable nonwoven fabric 12 which composes the top sheet 2 can be of a material made by a meltblown or spunbond process. Melt-spun stretchable fibers made from a thermoplastic elastomeric resin may be used as component fibers of the stretchable nonwoven fabric 12. A composite nonwoven fabric of which at least one side is the stretchable nonwoven fabric 12 comprising thermoplastic elastomeric resin fibers overlaid with a nonwoven fabric comprising melt-spun crimped fibers made from either of polypropylene, polyethylene and polyester thermoplastic synthetic resins may be used for the top sheet 2. An elastically contractible plastic film may be used for the top sheet 2.

Either of a hydrophobic nonwoven fabric and an air-permeable, liquid impervious plastic film may be used for the back sheet 3. A composite nonwoven fabric, of which at least one side comprises a meltblown nonwoven fabric of high water resistance, overlaid with a spunbonded nonwoven fabric of high strength and superior flexibility, may be used for the back sheet 3.

For the nonwoven fabrics 14 and 22 which form the back sheet 3, those made by spun lace, needle punch, meltblown, spunbond, chemical bond and airthrough processes may be used. Polyolefin, polyester and polyamide fibers as well as core-sheath type or parallel type bicomponent fibers made of polyethylene/polypropylene or polyethylene/polyester may be used as component fibers for the nonwoven fabrics 14 and 22.

An adhesive or thermal adhesion means, such as heat seal and sonic seal, may be used for joining the top sheet 2 and the back sheet 3 together, bonding the core 4 to the top sheet 2, joining together the film 13 and the nonwoven fabric 14 which together form the back sheet 3, and joining together the nonwoven fabrics 14 and 22 which together form the back sheet 3.

Hot-melt, acrylic and rubber-based adhesives may be used as adhesive means. The adhesives is applied in a spiral form to the top and back sheets 2 and 3, the film 13, and the nonwoven fabrics 14 and 22. When an adhesive is applied in a spiral form, an applied area in which the adhesive is applied and a non-applied area in which no adhesive is applied are formed. The adhesive may be applied, besides in a spiral form, in either of zigzag, dot and stripe form to the top and back sheets 2 and 3, the film 13, the nonwoven fabrics 14 and 22.

In the diapers 1A and 1B, no particular limitation is imposed on size and configurations of the upper and lower openings 10 and 11. In the diapers 1A and 1B, no particular limitation is imposed on the number of the upper and lower openings 10 and 11 either, and the upper opening 10 penetrating through the top sheet 2 in a thickness direction may be formed in the transversely middle zone 5a of the front waist region 5, and the lower opening 10 and 11 penetrating through the top sheet 2 and the core 4 in a thickness direction may be formed in the transversely middle zone 6a of the crotch region 6.

The present invention can be embodied in a pant-type diaper in which a waist opening and a pair of leg openings are formed with the pre-joined side flaps in the front and back regions, in addition to open-type diapers 1A and 1B in which the front and back waist regions are jointed when they are to be worn.

The disposable diaper according to the present invention allows the gathers formed in the free portion of the back sheet to extend by the weight of excrement and then the free portion to elongate downwards in a thickness direction of the diaper resulting in formation between the free portion and the core of a fecal material receiving space which is capable of containing excrement. If a large amount of excrement is discharged in the diaper while worn, the diaper is capable of containing such large amount of excrement in the space. This diaper ensures that the excrement can be prevented from soiling the crotch region of the wearer since the excrement will not stay on, nor be diffused over, the outer surface of the top sheet. This diaper is capable of spacing the excrement away from the crotch region of the wearer since the top sheet and the core are disposed between the excrement contained in the space and the crotch region of the wearer. In this diaper, the excrement will not pushed out of the space back to the outer surface of the top sheet if body pressure of the wearer is applied to the diaper as the top sheet and the core serve as a barrier to the excrement contained in the space.

The diaper having end flaps and side flaps a greater part of which comprises a stretchable/contractible top sheet is capable of fastening the waist and leg sections of the wearer by means of contracting force of the end and side flaps, by which the diaper can be prevented from sliding down from where it should be on the wearer and by which the body exudates are prevented from leaking from the gaps between the diaper and the legs of the wearer in both sides of the crotch region.

In a diaper whose back sheet gathers and pleats are formed, the gathers formed in the free portion of the back sheet extend in the longitudinal direction as a matter of course and the pleats expand in the transverse direction, so that the capacity of the fecal material containing space to be formed between the free portion and the core can further be increased, as compared with a diaper in which gathers only are formed in the back sheet, enabling to contain a larger amount of excrement in the space.

What is claimed is:

1. A disposable diaper, comprising:
   a top sheet facing the wearer;
   a liquid impervious back sheet facing away from the wearer;
   a liquid absorbent core disposed between said top and back sheets;
   a front waist region;
   a back waist region;
   a crotch region which is positioned between said front and back waist regions;
   end flaps which are outside respective end edges of said core and extend in a transverse direction of said diaper therefrom;
   side flaps which are outside respective side edges of said core and extend in said longitudinal direction of said diaper therefrom; and
   openings which pass through a thickness of said top sheet and said core and are formed in at least said crotch region out of said front and back waist regions and said crotch region;
   wherein said back sheet has a free portion which is underneath said core and extendible downwards in a thickness direction of said diaper, and fixed edge portions which defines an outer periphery of said free portion and fixed to said top sheet;
   wherein, of said free portion and said fixed edge portion, at least said free portion is contractibly attached with a plurality of elastic members which are arranged in said transverse direction of said diaper at a given interval; and
   wherein a plurality of gathers extending in said transverse direction are formed under contraction of said elastic members.

2. The disposable diaper of claim 1 wherein said top sheet is stretchable/contractible.

3. The disposable diaper of claim 1 wherein said back sheet is smaller in area than said top sheet and a greater part of said side flaps is formed out of the side portions of said top sheet which extend outwards from respective side edges of said core in said transverse direction.

4. The disposable diaper of claim 2 wherein a greater part of said end flaps is formed out of the end portions of said top sheet which extend outwards from respective end edges of said core in said longitudinal direction.

5. The disposable diaper of claim 1 wherein a longitudinal dimension of said back sheet, when said gathers are extended in said longitudinal direction against a contracting force of said elastic members, ranges 1.05 to 4.0 times a longitudinal dimension of said back sheet in a state in which the gathers are formed.

6. The disposable diaper of claim 1 wherein a tensile stress of said elastic member ranges 0.098 to 1.96 N when stretched to 100% of its initial length.

7. The disposable diaper of claim 1 wherein a plurality of pleats extending in said longitudinal direction are further formed in said back sheet by folding said back sheet in said transverse direction with said pleats being arranged at a given interval in said transverse direction.

8. The disposable diaper of claim 7 wherein a transverse dimension of said back sheet, when said pleats are extended in said transverse direction, ranges 1.5 to 3.0 times that of said back sheet in a state where said pleats are formed.

9. The disposable diaper of claim 1 said back sheet comprises one of a composite sheet made of a hydrophobic nonwoven fabric and a breathable but liquid impervious plastic film overlaid and joined together and a composite nonwoven fabric made of a plurality of hydrophobic nonwoven fabrics overlaid and joined together.

10. The disposable diaper of claim 1, wherein a portion of said backsheet is exposed through the openings in the topsheet and the absorbent core.

11. A disposable diaper, comprising:
    a topsheet adapted to face a wearer, in use;
    a liquid impervious backsheet adapted to face away from the wearer, in use;
    a liquid absorbent core disposed between said topsheet and backsheet;
    a front waist region;
    a rear waist region;
    a crotch region which extends in a longitudinal direction of said diaper between said front and rear waist regions; and
    first and second openings which pass through thicknesses of said topsheet and said core, respectively, and are formed in at least said crotch region to define a pocket for receiving therein bodily discharge;
    said backsheet having a portion which defines a bottom of said pocket, is exposed through the first and second openings of said topsheet and said core, and is elastically moveable in a downward direction away from said core to enlarge the pocket.

12. The disposable diaper of claim 11, further comprising a plurality of elastic members contractibly and directly attached to said portion of said backsheet at predetermined intervals, wherein
    when said elastic members are relaxed without being subject to external stretching forces, a plurality of gathers are formed in said portion of said backsheet under contraction of said elastic members; and
    said elastic members are elastically stretchable and render said portion of said backsheet elastically extensible in said downward direction.

13. The disposable diaper of claim 12, wherein said elastic members are elongated in the longitudinal direction of said diaper and are spaced from one another in a transverse direction of said diaper.

14. The disposable diaper of claim 11, wherein said backsheet is smaller in area than said topsheet and has fixed edges which surround said portion and are fixed to said topsheet.

15. The disposable diaper of claim 11, wherein said portion of said backsheet is elastically stretchable to have a longitudinal dimension in a range from 1.05 to 4.0 times a non-stretched longitudinal dimension of said portion of said backsheet when said portion of said backsheet is not stretched.

16. The disposable diaper of claim 11, wherein said portion of said backsheet is pleated.

17. The disposable diaper of claim 11, wherein a plurality of pleats extending in said longitudinal direction are further formed in said portion of said backsheet by folding said portion of said backsheet in a transverse direction of said diaper, said pleats being arranged at a given interval in said transverse direction.

18. The disposable diaper of claim 17, wherein a transverse dimension of portion of said backsheet when said portion of said backsheet is stretched to eliminate said pleats is in a range from 1.5 to 3.0 times a non-stretched transverse dimension of said portion of said backsheet when said portion of said backsheet is not stretched.

19. The disposable diaper of claim 11, wherein said first and second openings are different in at least one of shape and size; and an upper surface of said absorbent core, which faces the topsheet, is exposed through a first section of the first opening in the topsheet, whereas the portion of said backsheet is exposed through a different, second section of the first opening.

20. The disposable diaper of claim 11, wherein said first opening is the only opening extending through said topsheet, is elongated in the longitudinal direction, and further extends into the rear waist region.

* * * * *